United States Patent
Davis (10) Patent No.: US 7,245,972 B2
(45) Date of Patent: Jul. 17, 2007

(54) ELECTRICAL TREATMENT TO TREAT SHOULDER SUBLUXATION

(75) Inventor: Ross Davis, Melbourne Beach, FL (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 328 days.

(21) Appl. No.: 11/118,722

(22) Filed: Apr. 28, 2005

(65) Prior Publication Data

US 2005/0245989 A1    Nov. 3, 2005

Related U.S. Application Data

(60) Provisional application No. 60/567,111, filed on Apr. 29, 2004.

(51) Int. Cl.
*A61N 1/05* (2006.01)
(52) U.S. Cl. .......................... 607/118; 607/46
(58) Field of Classification Search ................. 607/46, 607/48, 50, 118
See application file for complete search history.

(56) References Cited

U.S. PATENT DOCUMENTS

| | | |
|---|---|---|
| 5,193,539 A | 3/1993 | Schulman et al. |
| 5,193,540 A | 3/1993 | Schulman et al. |
| 5,358,514 A | 10/1994 | Schulman et al. |
| 6,051,017 A | 4/2000 | Loeb et al. |
| 6,164,284 A | 12/2000 | Schulman et al. |
| 6,185,455 B1 | 2/2001 | Loeb et al. |
| 6,553,263 B1 | 4/2003 | Meadows et al. |
| 6,738,672 B2 | 5/2004 | Schulman et al. |
| 6,829,508 B2 | 12/2004 | Schulman et al. |

OTHER PUBLICATIONS

Loeb et al, Bion Implants for Therapeutic and Functional Electrical Stimulation, Neural Prostheses for Restoration of Sensory and Motor Function, 2001, pp. 75-99, Publisher: CRC Press, Published in: USA.

(Continued)

*Primary Examiner*—Carl Layno
*Assistant Examiner*—Yun Haeng Lee
(74) *Attorney, Agent, or Firm*—Malcolm J. Romano (57) ABSTRACT

A method for treating shoulder subluxation using an implantable device to stimulate the axillary nerve which in turn activates sensory fibers to relieve shoulder pain and activates deltoid muscle to treat disuse atrophy and possibly augment any weakened voluntary movements. Known stimulation devices are either (1) external requiring surface electrodes or (2) implantable located directly into the deltoid muscle allowing stimulation of the proximate motor-points; each requiring relatively large stimulus currents and neither directly dealing with the pain resulting from the shoulder subluxation. In the present invention, a device is implanted via injection or open surgery proximate to the axillary nerve. Advantageously, the nerve branches into portions that stimulate the deltoid muscle and pass sensory signals. By stimulating the axillary nerve (1) a lower stimulus signal level can be used and (2) pain may be blocked while treating the atrophied deltoid muscle and augmenting weakened voluntary movements.

21 Claims, 11 Drawing Sheets

OTHER PUBLICATIONS

Dupont et al, First Clinical Experience With Bion Implants for Therapeutic Electrical Stimulation, Jan. 2004, pp. 1-21, vol. 7, No. 1, Publisher: Neuromodulation, Published in: Los Angeles.

Misawa et al, The Use of the RF Bion Microstimulator to Relieve Pain Due to Shoulder Subluxation in Chronic Hemiplegic Stroke Patient, Sep. 2004, pp. 469-471, Publisher: 9th Annual Conference of the International FES Society, Published in: United Kingdom.

Shimada et al, RF Bion Microstimulator Implantation Technique for Shoulder Subluxation, Sep. 2004, pp. 475-477, Publisher: 9th Annual Conference of the International FES Society, Published in: United Kingdom.

ELECTRICAL TREATMENT TO TREAT SHOULDER SUBLUXATION

This application claims the benefit of U.S. Provisional Application No. 60/567,111, filed Apr. 29, 2004, the contents of which are incorporated herein by reference.

FIELD OF THE INVENTION

The present invention is generally directed to methods for treating shoulder subluxation, e.g., following a stroke, via the use of one or more medical devices configurable for implantation to stimulate the axillary nerve which in turn activates sensory fibers to relieve should pain and activates the deltoid muscle of the affected shoulder to treat the condition resulting from disuse atrophy and possibly augments weakened voluntary movements of the affected muscle and shoulder joint.

BACKGROUND OF THE INVENTION

Loss of upper motor control due to stroke results primarily in limb paralysis and secondarily in disuse atrophy of the affected muscle and shoulder joint. This atrophy may result in complications such as joint pain and skin breakdown, which may be even more troubling to the patient than the loss of motor function. Shoulder subluxation has been observed in 17% to 81% of hemiplegic patients. Muscle paresis around the shoulder joint decreases its stability and results in shoulder subluxation which is among the most commonly cited causes of shoulder pain in hemiplegia. It is difficult to treat these conditions even when traditional rehabilitation techniques and medicines are tried. Currently stimulating signals delivered via surface electrodes have been tried but are of limited use since they are not sufficiently close to the affected muscle to provide sufficient stimulation intensities for the necessary period of treatment. The use of multiple implanted devices is also known for directly stimulating multiple portions of the deltoid muscle. It is believed that such devices also require relatively high amplitude stimulation signals since they must directly stimulate muscle fibers and that they do not directly deal with the pain, until if and when the treatment is actually effective, which could be some period of time.

SUMMARY OF THE INVENTION

The present invention is generally directed to methods for treating shoulder subluxation and the ensuing pain, e.g., following a stroke, via the use of a medical device configurable for implantation to stimulate the axillary nerve which in turn activates sensory fibers to relieve should pain and activates the deltoid muscle of the affected shoulder to treat the condition resulting from disuse atrophy of the affected muscle and shoulder joint. Prior known devices are either (1) external stimulation devices requiring surface electrodes or (2) implantable devices which directly stimulate the proximate motor-points of affected deltoid muscle; each of which requiring relatively large stimulus currents and neither directly dealing with the pain resulting from the shoulder subluxation. In embodiments of the present invention, an internally implanted device, e.g., a BION® (a trademark of Advanced Bionics Corporation), is implanted (preferably via injection) proximate to the axillary nerve. Advantageously, the axillary nerve (one for each shoulder), originating from the C5/C6 vertebrae branch into anterior and posterior portions that both stimulate the deltoid muscle and pass sensory signals, e.g., pain, from the affected shoulder. By stimulating the axillary nerve (1) a lower stimulus signal level can be used to cause activation of the deltoid muscle and (2) this stimulus signal may also block pain while the effects of the atrophied deltoid muscle are being reversed; accordingly immediate and long term effects are provided.

Implanted devices in this exemplary environment may be configured similarly to the devices described in the commonly owned U.S. Pat. No. 6,164,284 (hereinafter referred to as the '284 patent), incorporated herein by reference in its entirety, and are typically contained within a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. Wireless communication between an external controller and optionally other implanted devices can be implemented in various ways, e.g., via a modulated sound signal, an AC magnetic field, an RF signal, a propagated electromagnetic wave, a light signal, or electrical conduction.

Alternatively, implanted devices in this exemplary environment may be configured similarly to the devices described in the commonly owned U.S. Pat. Nos. 5,193,539 and 5,193,540 (herein referred to as the '539 and '540 patents) each of which is incorporated herein by reference in its entirety. Such devices differ from those devices described in the '284 patent in that they do not contain a battery and instead rely upon an externally-provided AC magnetic field to induce a voltage, e.g., via a coil into an internal capacitor, and thus power its internal electronics only when the external AC magnetic field is present. These devices are also referred to as being RF powered. Systems which comprise the present invention may include either the '284 battery-powered or the '539/'540 RF-powered classes of devices or combinations thereof.

In accordance with the present invention, a preferred method for treating a patient with shoulder subluxation involving weakness and pain comprises the steps of (1) providing an implantable stimulator having at least two electrodes including a cathode and an anode, (2) implanting the stimulator via injection at an implantation site proximate to the axillary nerve of the shoulder to which treatment is directed, wherein the implantation site includes an area proximally where the axillary nerve originates to where the axillary nerve branches as the first fork of the anterior branch of the axillary nerve and preceding the first branch of the posterior branch of the axillary nerve where it branches into inferior and cutaneous branches, (3) providing at least one external controller for wireless transmission of stimulation parameters to the stimulator, and (4) delivering stimulation pulses in accordance with the transmitted stimulation parameters to the axillary nerve.

In a further aspect of embodiments of the present invention, the axillary nerve may be stimulated with one or more implantable devices proximate to various branches of the axillary nerve.

In a still further aspect of the present invention, the implantable devices may be coupled to the axillary nerve via a nerve cuff or other type of contact electrode.

The novel features of the invention are set forth with particularity in the appended claims. The invention will be best understood from the following description when read in conjunction with the accompanying drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
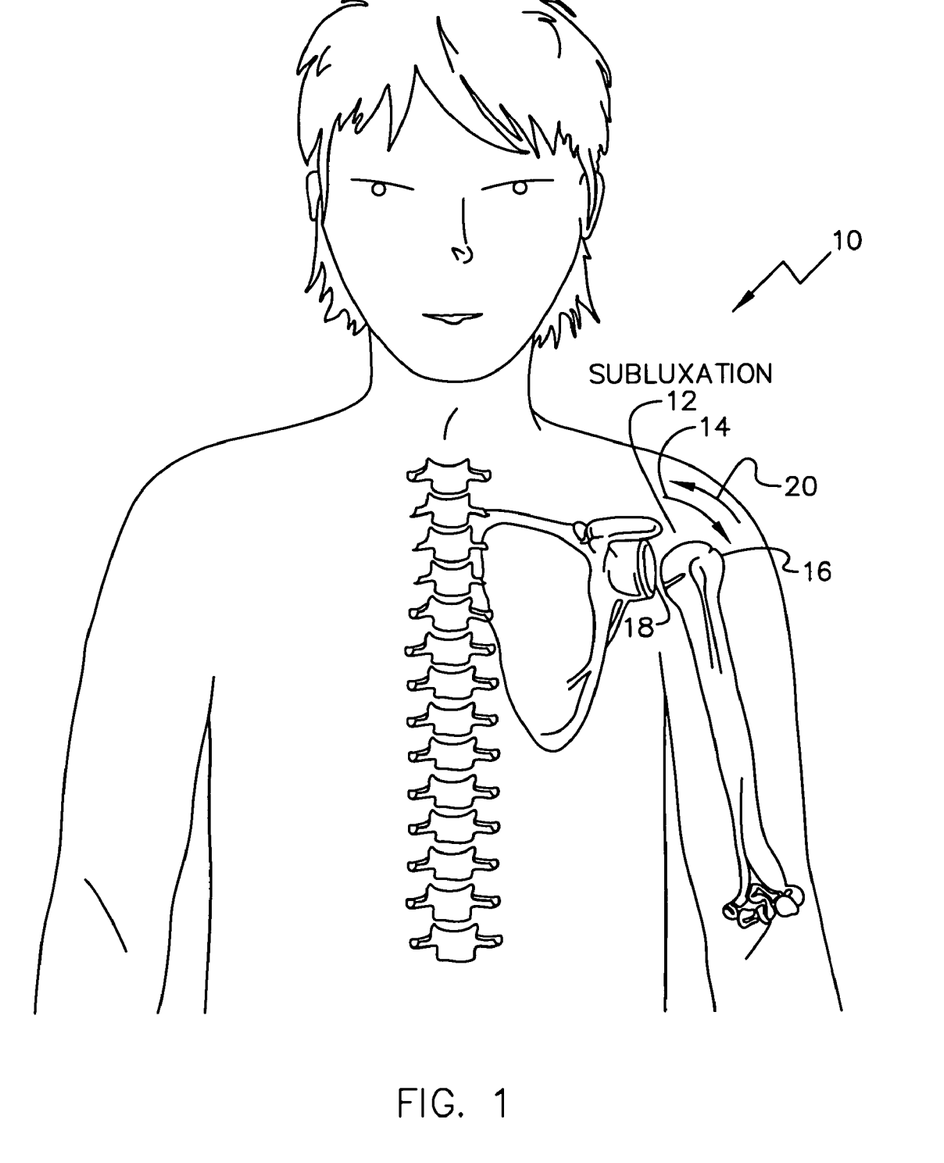
FIG. 1 is a simplified diagram of a patient who is experiencing shoulder subluxation, e.g., following a stroke, resulting in a downward movement primarily due to gravity which moves the ball portion downward from the socket portion of the shoulder joint.

The present invention is generally directed to methods for treating the pain and possible weakness/atrophy from shoulder subluxation, e.g., following a stroke, via the use of one or more medical devices configurable for implantation to stimulate the axillary nerve which in turn activates sensory fibers to relieve shoulder pain and activates the deltoid muscle of the affected shoulder to treat the condition resulting from disuse atrophy of the affected muscles and shoulder joint. As shown in FIG. 1, the exemplary patient 10 is experiencing shoulder subluxation of the shoulder joint 12, shown as a downward movement (vector 14) primarily due to gravity that pulls the ball portion 16 from the socket portion 18 of the shoulder joint 12. Following treatment with the present invention, the deltoid muscle surrounding the shoulder joint 12 is strengthened and an upward movement (vector 20) moves the ball 16 and socket 18 portions of the shoulder joint 12 back toward their nominal orientations. Prior known devices are either (1) external stimulation devices requiring surface electrodes or (2) implantable devices which directly stimulate the proximate motor-points of the affected deltoid muscle; each of which requiring relatively large stimulus currents and may not directly deal with the pain resulting from the shoulder subluxation. In embodiments of the present invention, an internally implanted device, e.g., a BION® (a trademark of Advanced Bionics Corporation), is implanted (preferably via injection) proximate to the axillary nerve. Advantageously, the axillary nerve (one for each shoulder), originating from the C5/C6 vertebrae branch into anterior and posterior portions that both activates the deltoid muscle and passes sensory signals, e.g., pain, from the affected shoulder. By stimulating the axillary nerve (1) a lower stimulus signal level can be used, (2) pain may be blocked while the effects of the atrophied deltoid muscle are being reversed, and (3) voluntary shoulder movements may be augmented; accordingly immediate and long term effects are provided.

Implanted devices in this exemplary environment may be configured similarly to the devices described in the commonly owned U.S. Pat. No. 6,164,284 (hereinafter referred to as the '284 patent), incorporated herein by reference in its entirety, and are typically contained within a sealed housing suitable for injection into the patient's body. Each housing preferably contains a power source having a capacity of at least 1 microwatt-hour and power consuming circuitry preferably including a data signal transmitter and receiver and sensor/stimulator circuitry for driving an input/output transducer. Wireless communication between an external controller and optionally other implanted devices can be implemented in various ways, e.g., via a modulated sound signal, a modulated AC magnetic field, an RF signal, a propagated electromagnetic wave, a light signal, or electrical conduction.

Alternatively, implanted devices in this exemplary environment may be configured similarly to the devices described in the commonly owned U.S. Pat. Nos. 5,193,539 and 5,193,540 (herein referred to as the '539 and '540 patents) each of which is incorporated herein by reference in its entirety. Such devices differ from those devices described in the '284 patent in that they do not contain a battery and instead rely upon an externally-provided AC magnetic field to induce a voltage, e.g., via a coil into an internal capacitor, and thus power its internal electronics only when the external AC magnetic field is present. These devices are also referred to as being RF powered. Systems which comprise the present invention may include either the '284 battery-powered or the '539/'540 RF-powered classes of devices or combinations thereof.

Figure 2:
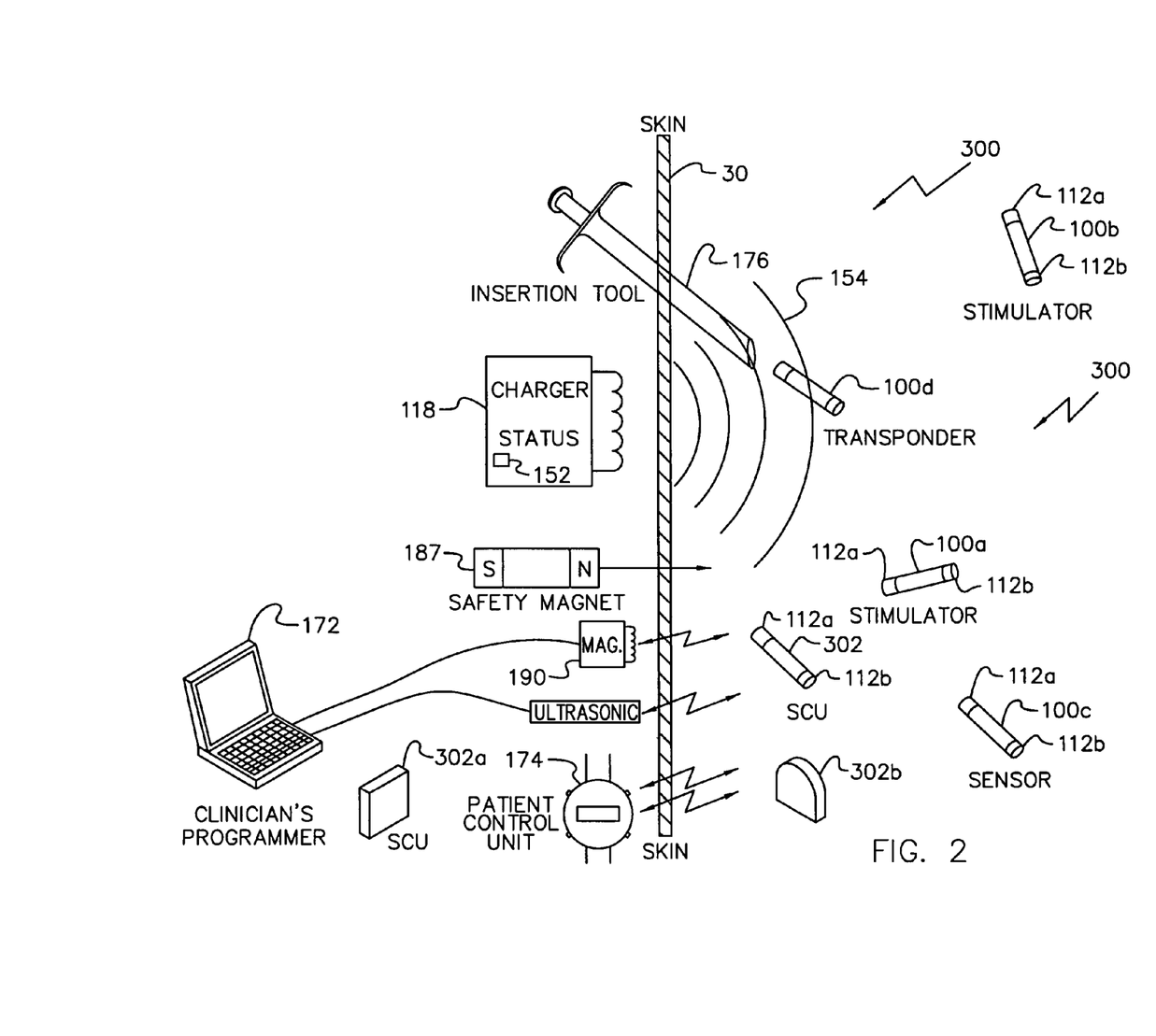
FIG. 2 is a simplified block diagram of an exemplary system suitable for practicing the present invention, the system being comprised of implanted devices, e.g., microstimulators, microsensors and microtransponders, under control of a system control unit (SCU).
Figure 3:
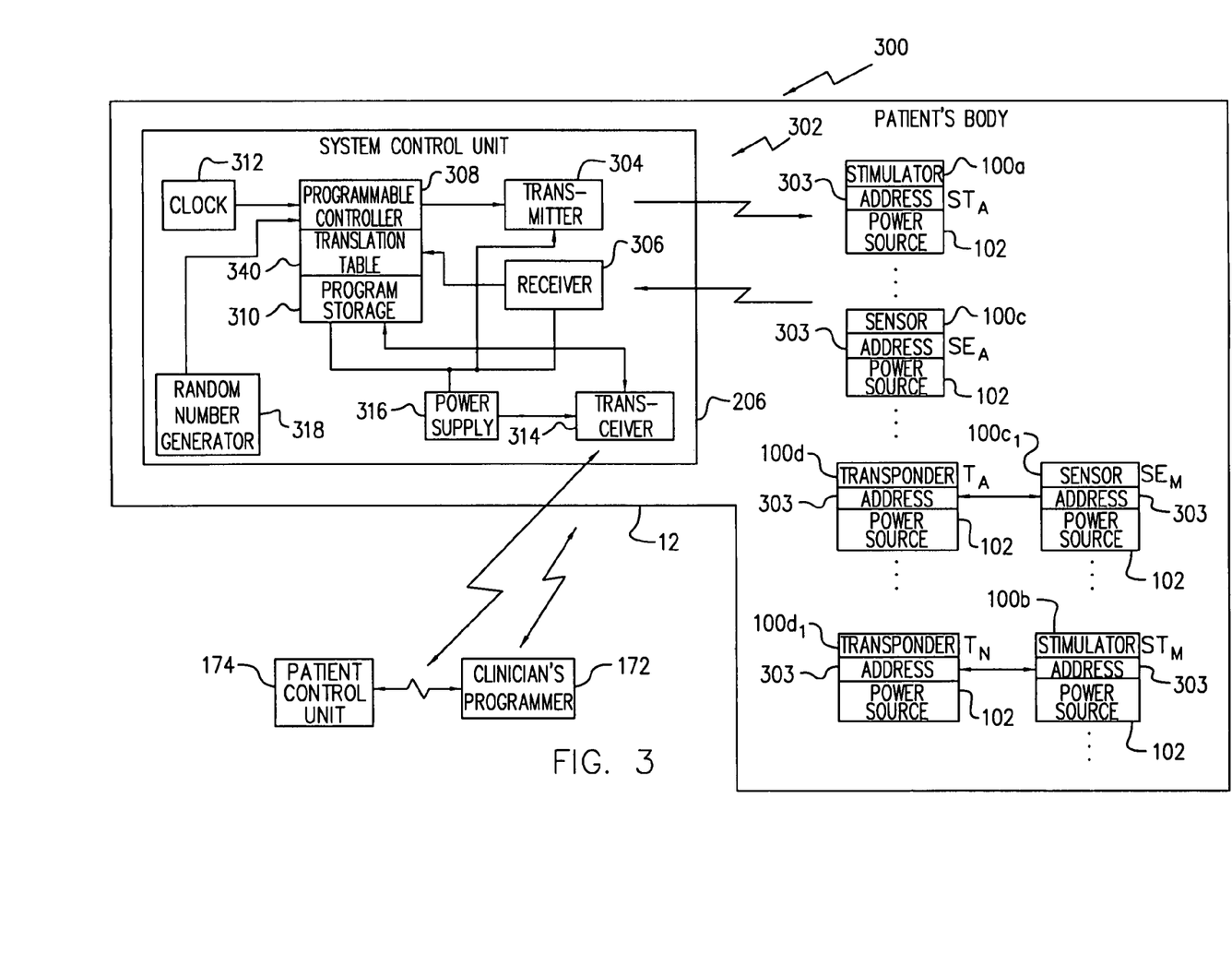
FIG. 3 comprises a block diagram of the system of FIG. 2 showing the functional elements that form the system control unit and implanted microstimulators, microsensors and microtransponders.

FIGS. 2 and 3 show an exemplary system 300 made of implanted devices 100, preferably battery powered, under control of a system control unit (SCU) 302, preferably also implanted beneath a patient's skin 30. As described in the '284 patent, potential implanted devices 100 include stimulators, e.g., 100a and 100b, sensors, e.g., 100c, and transponders, e.g., 100d. The stimulators, e.g., 100a, can be remotely programmed to output a sequence of drive pulses to body tissue proximate to its implanted location via attached electrodes 112a, 112b. The sensors, e.g., 100c, can be remotely programmed to sense one or more physiological or biological parameters in the implanted environment of the device, e.g., temperature, glucose level, $O_2$ content, nerve potential, muscle potential, etc. Transponders, e.g., 100d, are devices which can be used to extend the interbody communication range between stimulators and sensors and other devices, e.g., a clinician's programmer 172 and the patient control unit 174. Preferably, these stimulators, sensors and transponders are contained in sealed elongate housings having an axial dimension of less than 60 mm and a lateral dimension of less than 6 mm. Accordingly, such stimulators, sensors and transponders are respectively referred to as microstimulators, microsensors, and microtransponders or referred to in general as battery-powered, implantable stimulator/sensor devices. Such microstimulators and microsensors can thus be positioned beneath the skin 30 within a patient's body using a hypodermic type insertion tool 176.

As described in the '284 patent, microstimulators and microsensors are remotely programmed and interrogated via a wireless communication channel, e.g., modulated AC magnetic, sound (i.e., ultrasonic), RF or electric fields, typically originating from control devices external to the patient's body, e.g., the clinician's programmer 172 or patient control unit 174. Typically, the clinician's programmer 172 is used to program a single continuous or one time pulse sequence into each microstimulator and/or measure a biological parameter from one or more microsensors. Similarly, the patient control unit 174 typically communicates with the implanted devices 100, e.g., microsensors 100c, to monitor biological parameters. In order to distinguish each implanted device over the communication channel, each implanted device is manufactured with a unique address or identification code (ID) 303 specified in address storage circuitry 108 (see FIG. 4A) as described in the '284 patent. Unique is a relative term, e.g., the more bits used to specify the identification code the easier it will be to distinguish one device or, in the case of master devices, one system of devices from another system of devices. Accordingly, as used in this patent application, unique is only intended to specify that the ID 303 is distinguishable from the IDs of other devices that may exist within the same environment.

By using one or more such implantable devices in conjunction with the SCU 302, the capabilities of such implanted devices can be further expanded. For example, in an open loop mode, the SCU 302 can be programmed to periodically initiate tasks, e.g., perform real time tasking, such as transmitting commands to microstimulators according to a prescribed treatment regimen or periodically monitor biological parameters to determine a patient's status or the effectiveness of a treatment regimen. Alternatively, in a closed loop mode, the SCU 302 may periodically interrogate one or more microsensors and accordingly adjust the commands transmitted to one or more microstimulators.

FIG. 3 shows an exemplary system 300 comprised of (1) one or more implantable devices 100 operable to sense and/or stimulate a patient's body parameter in accordance with one or more controllable operating parameters and (2) the SCU 302. The SCU 302 is primarily comprised of (1) a housing 206, preferably sealed and configured for implantation beneath the skin of the patient's body, e.g., as described in the '284 patent in reference to the implanted devices 100, (2) a signal transmitter 304 in the housing 206 for transmitting command signals, (3) a signal receiver 306 in the housing 206 for receiving status signals, and (4) a programmable controller 308, e.g., a microcontroller or state machine, in the housing 206 responsive to received status signals for producing command signals for transmission by the signal transmitter 304 to other implantable devices 100. The sequence of operations of the programmable controller 308 is determined by an instruction list, i.e., a program, stored in program storage 310, coupled to the programmable controller 308. While the program storage 310 can be a nonvolatile memory device, e.g., ROM, manufactured with a program corresponding to a prescribed treatment regimen, it is preferable that at least a portion of the program storage 310 be an alterable form of memory, e.g., RAM, EEPROM, etc., whose contents can be remotely altered as described further below. However, it is additionally preferable that a portion of the program storage 310 be nonvolatile so that a default program is always present. The rate at which the program contained within the program storage 310 is executed is determined by clock/oscillator 312. Additionally, a real time clock operating in response to clock/oscillator 312 preferably permits tasks to be scheduled at specified times of day.

The signal transmitter 304 and signal receiver 306 preferably communicate with implanted devices 100 using an RF signal, e.g., a propagated electromagnetic wave, modulated by a command data signal. Alternatively, an audio transducer may be used to generate mechanical vibrations having a carrier frequency modulated by a command data signal. In an exemplary embodiment, a carrier frequency of 100 kHz or greater, e.g., 128 KHz, 2 MHz, etc., is used which corresponds to a frequency that freely passes through a typical body's fluids and tissues. However, such sound means that operate at any frequency, e.g., greater than 1 Hz, are also considered to be suitable for a potential communication channel. Alternatively, the signal transmitter 304 and signal receiver 306 can communicate using modulated AC magnetic fields.

The clinician's programmer 172 and/or the patient control unit 174 and/or other external control devices can also communicate with the implanted devices 100, as described in the '284 patent, preferably using a modulated RF or AC magnetic field. Alternatively, such external devices can communicate with the SCU 302 via a transceiver 314 coupled to the programmable controller 308. Since, the signal transmitter 304 and signal receiver 306 may operate using a different communication means, a separate transceiver 314 which operates using an alternative communication means may be used for communicating with external devices. However, a single transmitter 304/receiver 306 can be used in place of transceiver 314 for communicating with the external devices and implanted devices if a common communication channel is used.

Figure 4A:
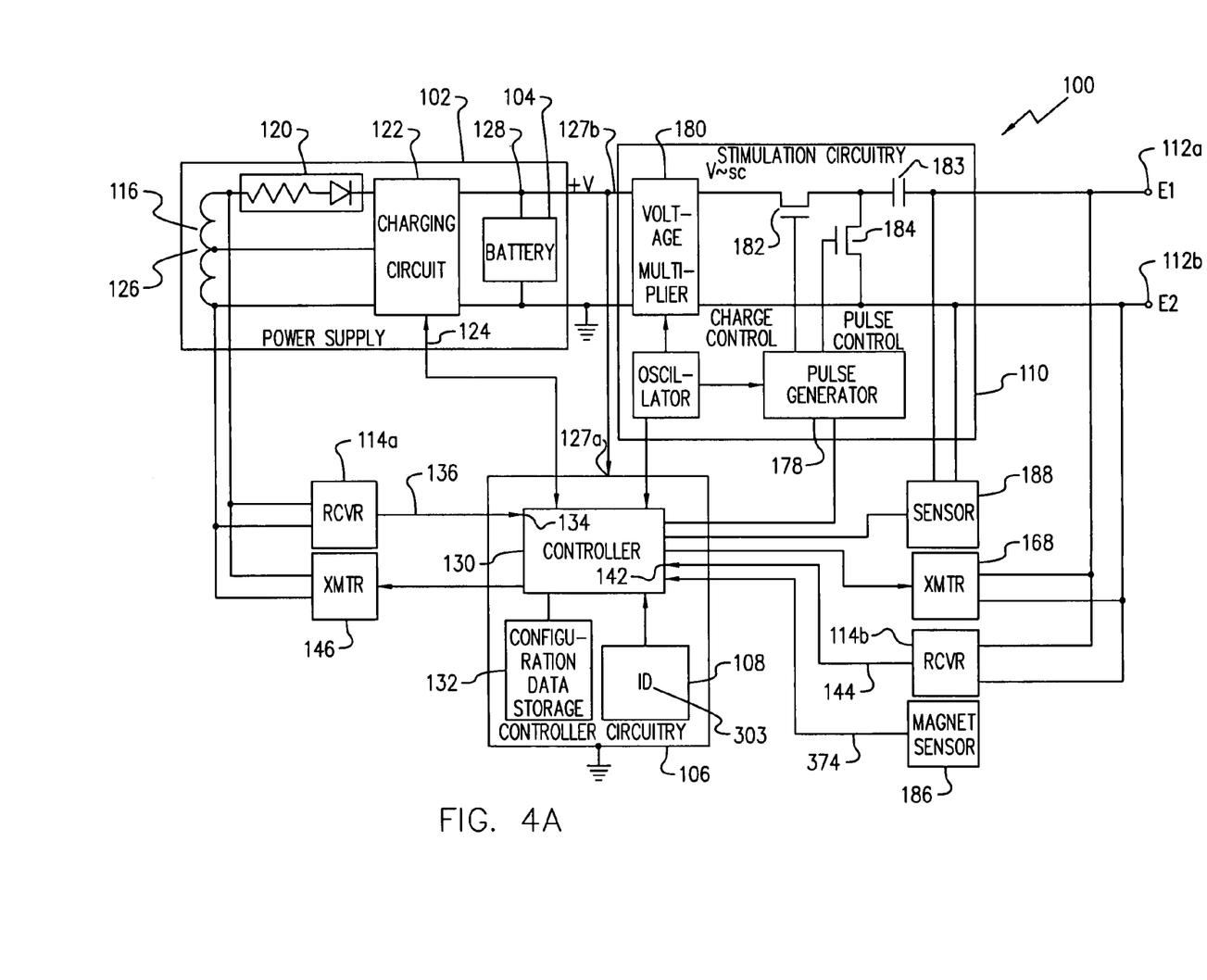
FIG. 4A comprises a block diagram of an exemplary implantable device, as shown in U.S. Pat. No. 6,164,284, including a battery for powering the device for a period of time in excess of one hour in response to a command from the system control unit.
Figure 4B:
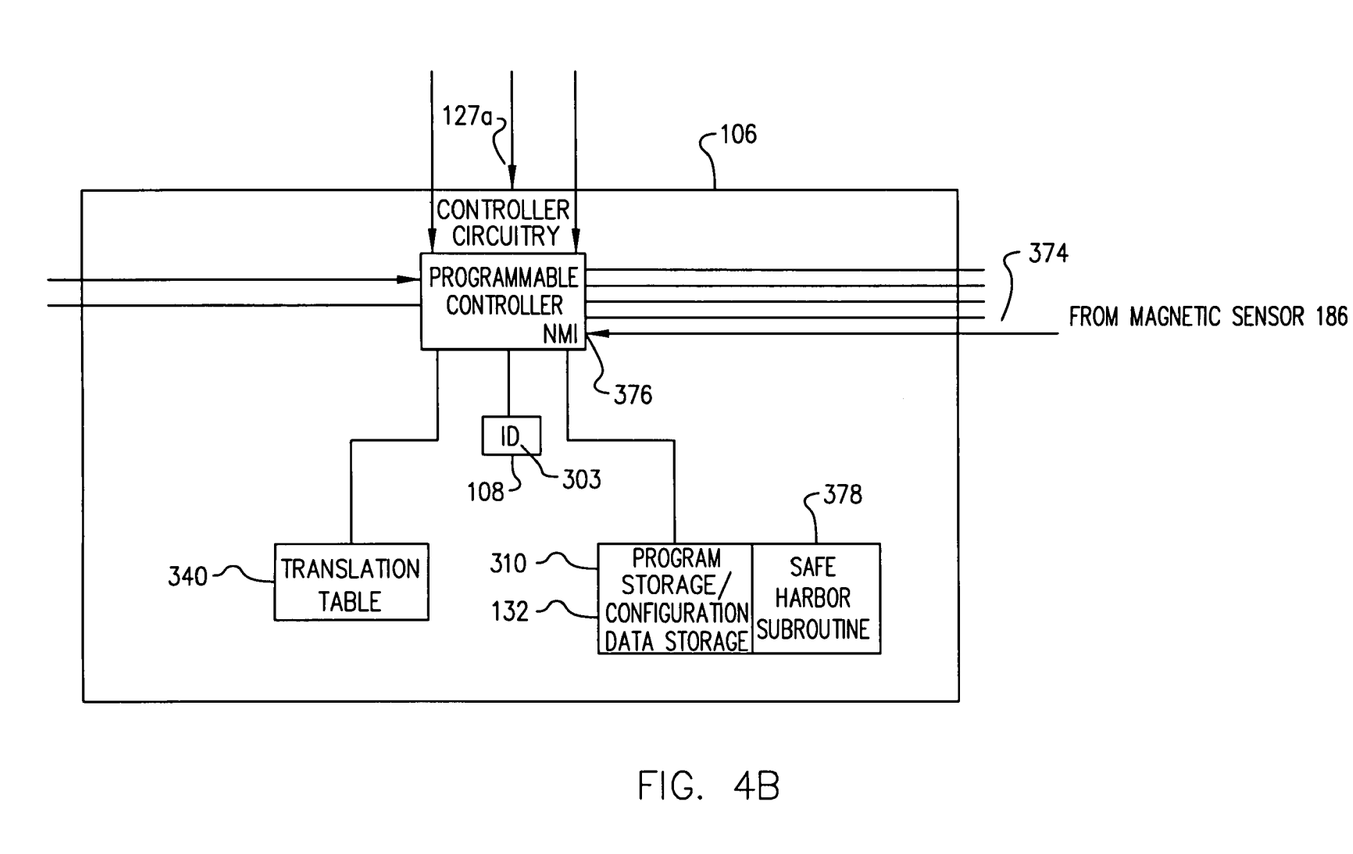
FIG. 4B comprises a simplified block diagram of controller circuitry that can be substituted for the controller circuitry of FIG. 4A, thus permitting a single device to be configured as a system control unit and/or a microstimulator and/or a microsensor and/or a microtransponder.

FIG. 4A comprises a block diagram of an exemplary implantable device 100 operable under control of controller circuitry 106 and includes a battery 104, preferably rechargeable, for powering the device for a period of time in excess of one hour and responsive to command signals from a remote master device, e.g., the SCU 302. The controller circuitry 106 is primarily comprised of a controller 130, configuration data storage 132 for prescribing its operation, and address storage circuitry 108 for storing the ID 303 of the device. As described in the '284 patent, the implantable device 100 is preferably configurable to alternatively operate as a microstimulator and/or microsensor and/or microtransponder due to the commonality of most of the circuitry contained within. Such circuitry may be further expanded to permit a common block of circuitry to also perform the functions required for the SCU 302. Accordingly, FIG. 4B shows an alternative implementation of the controller circuitry 106 of FIG. 4A that is suitable for implementing a microstimulator and/or a microsensor and/or a microtransponder and/or the SCU 302. In this implementation, the configuration data storage 132 can be alternatively used as the program storage 310 when the implantable device 100 is used as the SCU 302. In this implementation, XMTR 168 corresponds to the signal transmitter 304 and the RCVR 114b corresponds to the signal receiver 306 (preferably operable via electrodes 112a and 112b operating as an RF antenna) and the RCVR 114a and XMTR 146 correspond to the transceiver 314 (preferably operable via coil 116 for AC magnetic modes of communication).

Preferably, the contents of the program storage 310, i.e., the software that controls the operation of the programmable controller 308, can be remotely downloaded, e.g., from the clinician's programmer 172 using data modulated onto an RF signal or an AC magnetic field. In this mode, it is preferable that the contents of the program storage 310 for each implantable device be protected from an inadvertent change. Accordingly, the contents of the address storage circuitry 108, i.e., the ID 303, is preferably used as a security code to confirm that the new program storage contents are destined for the implantable device receiving the data. This feature is particularly significant if multiple patients could be physically located, e.g., in adjoining beds, within the communication range of the clinician's programmer 172.

Preferably, the implantable device can operate for an extended period of time, e.g., in excess of one hour, from an internal power supply 316 (see FIG. 3). While a primary battery, i.e., a nonrechargeable battery, is suitable for this function, it is preferable that the power supply 316 include a rechargeable battery, e.g., battery 104 as described in the '284 patent, that can be recharged via an AC magnetic field produced external to the patient's body.

The battery-powered devices 100 of the '284 patent are preferably configurable to operate in a plurality of operational modes, e.g., via a communicated command signal. In a first operational mode, device 100 is remotely configured to be a microstimulator, e.g., 100a and 100b. In this embodiment (see FIG. 4A), controller 130 commands stimulation circuitry 110 to generate a sequence of drive pulses through electrodes 112, i.e., a cathode electrode and an anode electrode, to stimulate tissue, e.g., a nerve or muscle, proximate to the implanted location of the microstimulator, e.g., 100a or 100b. In operation, a programmable pulse generator 178 and voltage multiplier 180 are configured with parameters corresponding to a desired pulse sequence and specifying how much to multiply (or divide) the battery voltage (e.g., by summing charged capacitors or similarly charged battery portions) to generate a desired compliance voltage $V_c$. A first FET 182 is periodically energized to store charge into capacitor 183 (in a first direction at a low current flow rate through the body tissue) and a second FET 184 is periodically energized to discharge capacitor 183 in an opposing direction at a higher current flow rate which stimulates a nearby muscle or nerve. Alternatively, electrodes can be selected that will form an equivalent capacitor within the body tissue.

In a next operational mode, the battery-powered implantable device 100 can be configured to operate as a microsensor, e.g., 100c, that can sense one or more physiological or biological parameters in the implanted environment of the device. In accordance with a preferred mode of operation, the system control unit 302 periodically requests the sensed data from each microsensor 100c using its ID 303 stored in the address storage circuitry 108, and responsively sends command signals to microstimulators, e.g., 100a and 100b, adjusted according to the sensed data. For example, sensor circuitry 188 can be coupled to the electrodes 112 to sense or otherwise used to measure a biological parameter, e.g., temperature, glucose level, $O_2$ content, voltage, current, impedance, etc., and provide the sensed data to the controller circuitry 106. Preferably, the sensor circuitry 188 includes a programmable bandpass filter and an analog to digital (A/D) converter that can sense and accordingly convert the voltage levels across the electrodes 112 into a digital quantity. Alternatively, the sensor circuitry 188 can include one or more sense amplifiers to determine if the measured voltage exceeds a threshold voltage value or is within a specified voltage range. Furthermore, the sensor circuitry 188 can be configurable to include integration circuitry to further process the sensed voltage. The operational mode of the voltage sensor circuitry 188 is remotely programmable via the device's communication interface.

Additionally, the sensing capabilities of a microsensor preferably include the capability to monitor the battery status via path 124 from the charging circuit 122 and can additionally include using an ultrasonic transducer, i.e., emitter/receiver (not shown), or the coil 116 to respectively measure the ultrasonic, magnetic or propagated RF signal magnitudes (or communication time delays) of signals transmitted between a pair of implanted devices and thus determine the relative locations of these devices. This information can be used to determine the amount of body movement, e.g., the amount that an elbow or finger is bent, and thus form a portion of a closed loop motion control system. See, for example, commonly assigned U.S. Provisional Patent Application No. 60/497,419, entitled "Goniometry" and its progeny U.S. patent application Ser. No. 10/920,554 which are incorporated herein by reference in their entirety.

In another operational mode, the battery-powered implantable device 100 can be configured to operate as a microtransponder, e.g., 100d. In this operational mode, the microtransponder receives (via the aforementioned RCVR 114a using AC magnetic, sonic, RF, or electric communication modes) a first command signal from the SCU 302 and retransmits this signal (preferably after reformatting) to other implanted devices (e.g., microstimulators, microsensors, and/or microtransponders) using the aforementioned XMTR 168 using magnetic, sonic, RF, or electric communication modes. While a microtransponder may receive one mode of command signal, e.g., magnetic, it may retransmit the signal in another mode, e.g., RF. For example, clinician's programmer 172 may emit a modulated magnetic signal using a magnetic emitter 190 (see FIG. 2) to program/command the implanted devices 100. However, the magnitude of the emitted signal may not be sufficient to be successfully received by all of the implanted devices 100. As such, a microtransponder 100d may receive the modulated magnetic signal and retransmit it (preferably after reformatting) as a modulated ultrasonic or RF signal which can pass through the body with fewer restrictions. In another exemplary use, the patient control unit 174 may need to monitor a microsensor 100c in a patient's foot. Despite the efficiency of ultrasonic, magnetic, and propagated RF communication in a patient's body, such a signal could still be insufficient to pass from a patient's foot to a patient's wrist (the typical location of the patient control unit 174). As such, a microtransponder 100d could be implanted (if needed) in the patient's torso to improve the communication link.

Referring again to FIG. 4A, a magnetic sensor 186 is shown. In the '284 patent, it was shown that such a sensor 186 could be used to disable the operation of an implanted device 100, e.g., to stop or otherwise alter the operation of such devices in an emergency situation, in response to a DC magnetic field, preferably from an externally positioned safety magnet 187 (see FIG. 2). Additionally, it is noted that power to at least some portions of a preferred implantable device may be removed when a magnetic field is sensed and thus power may be conserved. The magnetic sensor 186 can be implemented using various devices. Exemplary of such devices are devices manufactured by Nonvolatile Electronics, Inc. (e.g., their AA, AB, AC, AD, or AG series), Hall effect sensors, magnetoresistive sensors, and subminiature reed switches. Such miniature devices are configurable to be placed within the housing of the SCU 302 and implantable devices 100. While essentially passive magnetic sensors, e.g., reed switches, are possible, the remaining devices may include active circuitry that consumes power during detection of the DC magnetic field. Accordingly, it is preferred that controller 130 periodically, e.g., once a second, provide power to the magnetic sensor 186 and sample the magnetic sensor's output signal 374 during that sampling period. Additionally, a magnetoresistive sensor is especially preferred due to its small size that enables its use within the preferred implantable device 100 while conserving the available internal package volume.

The battery 104 used for powering the implantable device 100 (or SCU 302) is made from appropriate materials so as to preferably provide a power capacity of at least 1 microwatt-hour. Preferably, such a battery, e.g., a Li—I battery, has an energy density of about 240 mw-Hr/cm$^3$. The battery voltage V of an exemplary battery is nominally 3.6 volts, which is more than adequate for operating the CMOS circuits preferably used to implement the IC chip(s) 216, and/or other electronic circuitry, within the SCU 302.

The battery 104 may take many forms, any of which may be used so long as the battery can be made to fit within the small volume available. The battery 104 may be either a primary battery or a rechargeable battery. A primary battery offers the advantage of not requiring a recharging circuit and the disadvantage of not being rechargeable (which means once its energy has been used up, the implanted device no longer functions). Alternatively, as described within this application, RF-powered devices are also applicable to embodiments of the present invention.

Essentially, there have been described two classes of implantable devices 100, a first which is typically referred to as being RF powered, i.e., it does not contain a battery but instead receives all of its operating power from an externally-provided AC magnetic field (which field is preferably modulated to additionally wirelessly communicate commands to the implantable devices 100), and a second class which is referred to as battery powered which is powered by an internally provided battery which, in turn, is preferably rechargeable and periodically recharged by a similar externally-provided AC magnetic field (see, for example, commonly assigned U.S. Patent Application Publication No. 2003/0078634 corresponding to U.S. patent application Ser. No. 10/272,229, which is incorporated herein by reference in its entirety, which describes recharging environments, e.g., a chair, bed, etc., and techniques for use with such implantable devices) but preferably receives its wireless commands via a modulated RF signal. Alternatively, as shown further below (see FIG. 7), a system 400 is shown having an external harness 402 mounted to the patient's body proximate to the implantable device 100 to provide power and/or control signals under control of a coupled external controller 404 that includes the functionality of the charger 118, clinician's programmer 172, patient control unit 174, or the like, which provides power/control signals to the external harness 402 (see, for example, the aforementioned '539 and '540 patents). Thus, in this case, the wireless command signal may be distinct from the wireless charging signal. However, in most other ways, these two classes of implantable devices 100 are similar, e.g., they have similar size restrictions, are suitable for implantation via injection, and can similarly stimulate neural pathways and, thus, they are accordingly generally interchangeable in embodiments of the present invention. Alternatively, embodiments of the present invention may include combinations of RF and battery-powered devices (e.g., essentially the device of the '284 patent without a battery but solely a capacitor in its place to temporarily capture and provide power to the device as described in the '539/'540 patents) to take advantage of differences, e.g., cost and functional, between both classes of devices.

Figure 5:
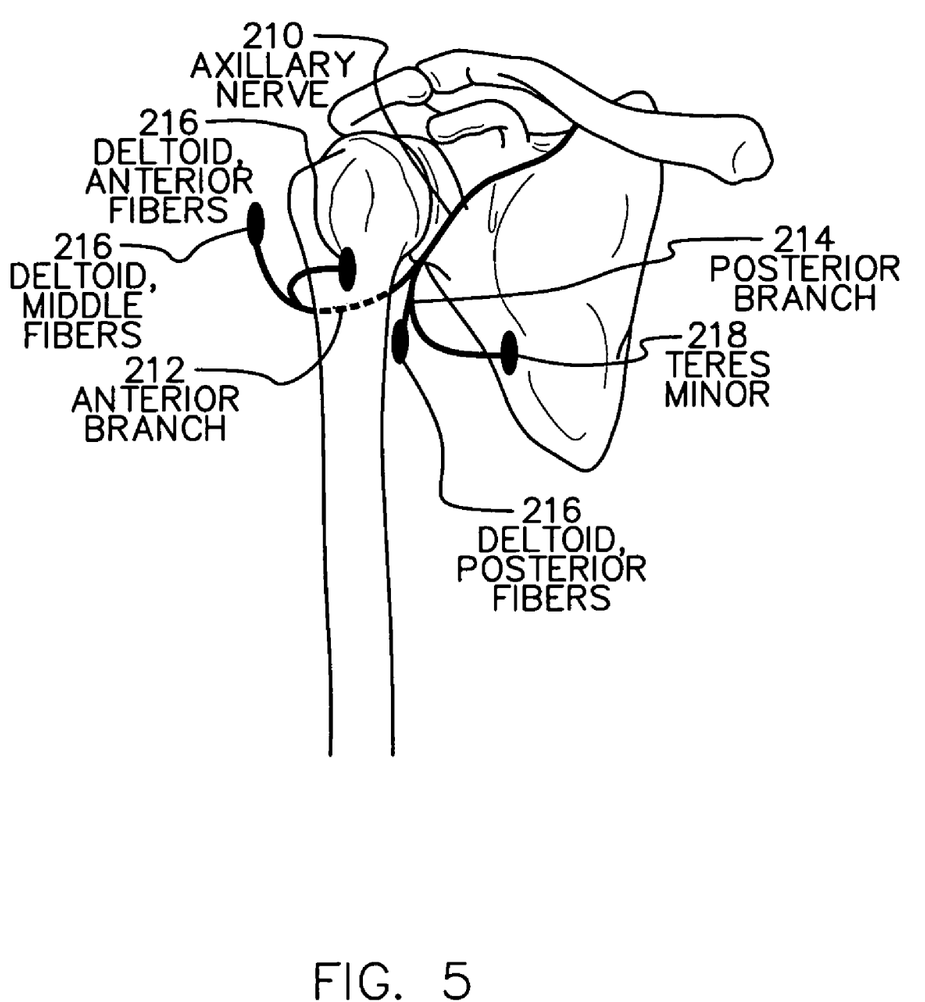
FIG. 5 shows a simplified diagram of the pathways of various branches of the axillary nerve to various portions of the deltoid muscle.
Figure 6:
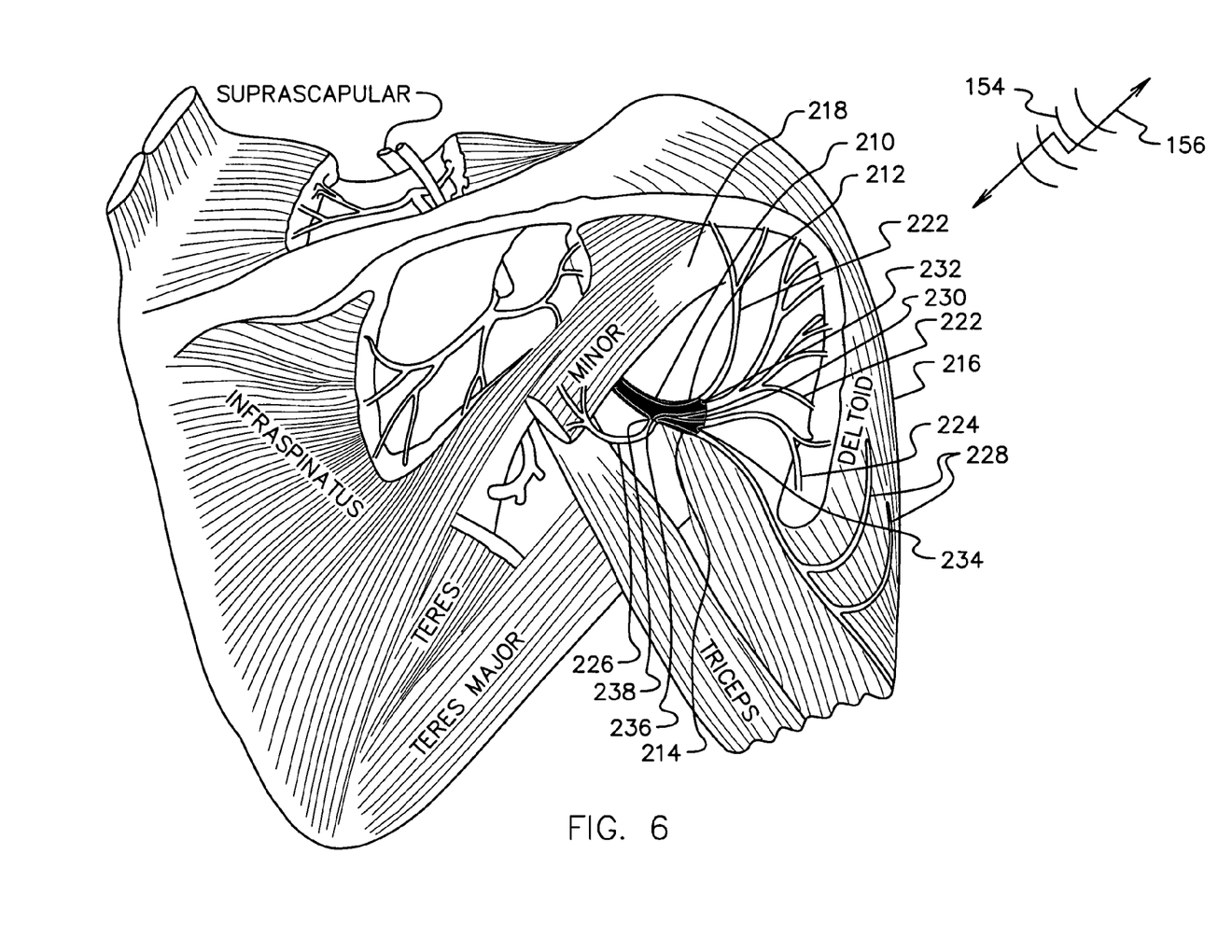
FIG. 6 shows a more detailed diagram of the anatomy of a patient's shoulder showing the motor and sensory branches of the axillary nerve to various portions of the deltoid muscle.

FIG. 5 shows a simplified diagram of the pathways of anterior 212 and posterior 214 branches of the axillary nerve 210 to various portions of the deltoid muscle 216 and the sensory areas of the shoulder (also see FIG. 6 which additionally shows the anterior 212 branch forking into superior branches 222 and the posterior 214 branch forking into inferior branches 224 and a nerve 226 to the teres minor 218). Advantageously, the branches 212, 214 which then go to the deltoid muscle 216 are part of the targets for the treatment of the present invention (teres minor 218 involvement is not considered to be neither necessary nor detrimental to this treatment). Accordingly, as shown in FIG. 6, a more detailed diagram of the anatomy of a patient's shoulder, a target stimulation area is shown within a shaded target oval shaped area 230 and extending proximally where the nerve originates. This target stimulation oval shaped area 230 includes the areas proximate to the axillary nerve 210 that precede the first fork 232 of the anterior branch 212 of the axillary nerve 210 and precede the first fork 234 of the posterior branch 214 of the anterior nerve 210 where it branches into inferior 224 and cutaneous branches 228. By placing a single implantable device 100 across the shown axillary branches in the target oval shaped area 230 (see FIG. 8), currents can pass through the targeted anterior 212 and posterior 214 branches of the axillary nerve 210 and thus periodically activate the deltoid muscle 216 to contract. Advantageously, the required current level to stimulate the axillary nerve 210 and consequently activate the deltoid muscle 216 is much lower with this approach, permitting the use of a battery-powered implantable device (operating independently following charging and programming as described in the '284 patent). Advantageously, such battery-powered devices may also be able to provide sub clinical stimulation pulses, i.e., pulses that are not sufficient to cause depolarization of the deltoid muscle but may still be able to stimulate the sensory nerves to block or decrease pain in the patient's shoulder. Additionally, RF-powered implantable devices 100 which are powered and controlled via external system 400 comprised of harness 402 mounted over the patient's shoulder and external controller 404 (see FIG. 7) may be used. In such an embodiment, the external controller 404 is directly coupled to the harness 402 which includes a coil 406 for providing an AC magnetic field (preferably modulated with control information). Alternatively, an RF signal could provide the control information. The external controller 402 may contain an internal rechargeable battery (not shown) which preferably operates off of an external battery charger 408 or may operate directly off of an AC power source (that need only be present during treatment periods). Preferably, the external controller 404 is programmable via a communication link 410 (typically via a cable) with the clinician's programmer 172 (or the like) or may be programmable via an on-board control/switch panel (not shown).

Figure 7:
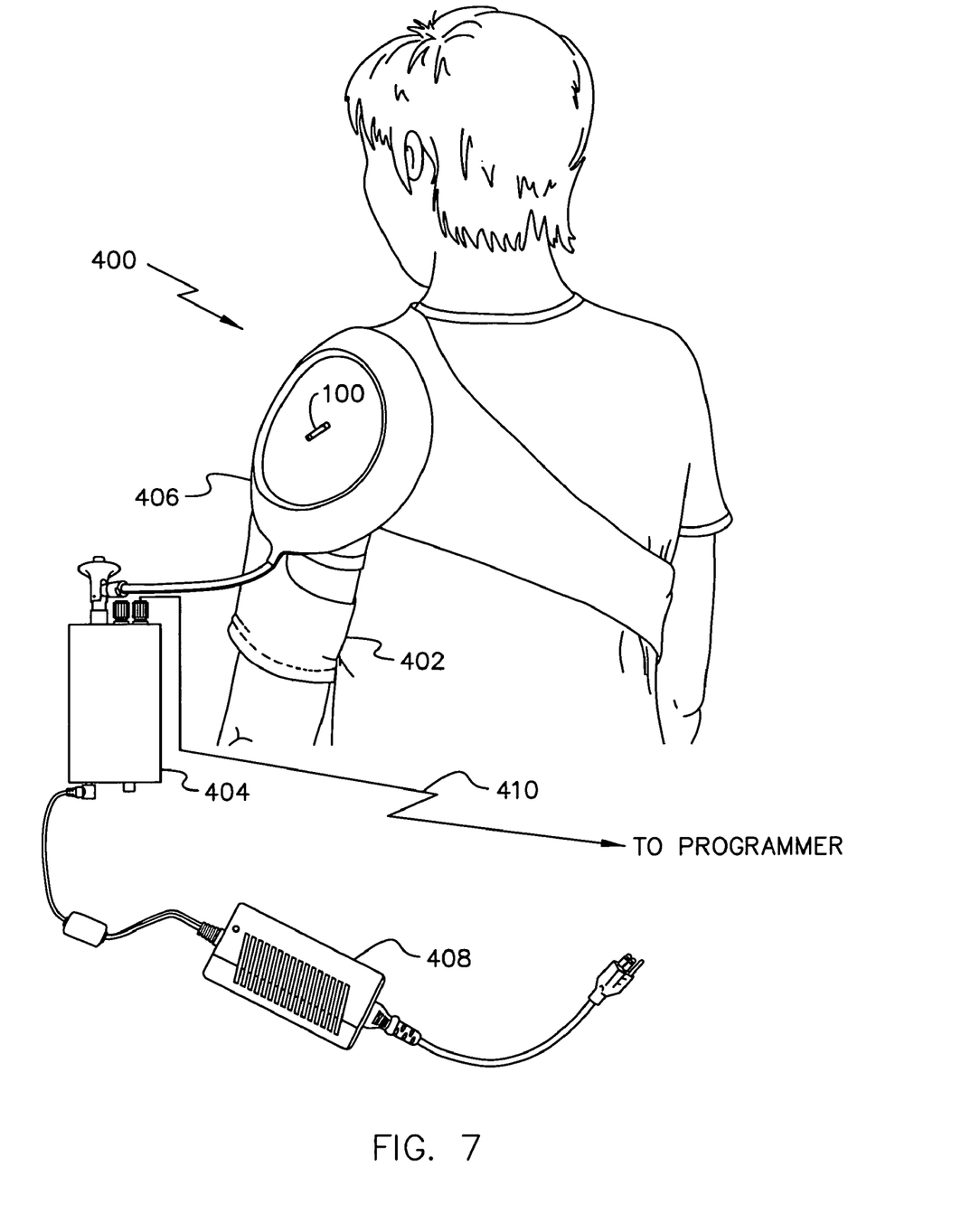
FIG. 7 shows the use of an external control system comprised of a harness that mounts a coil proximate to the implanted device in the patient's shoulder. The coil is coupled to an external controller that supplies an AC magnetic field to supply operating and/or charging power to the implantable device. Additionally, the external device preferably supplies control information to the implanted device to control the treatment parameters.
Figure 8:
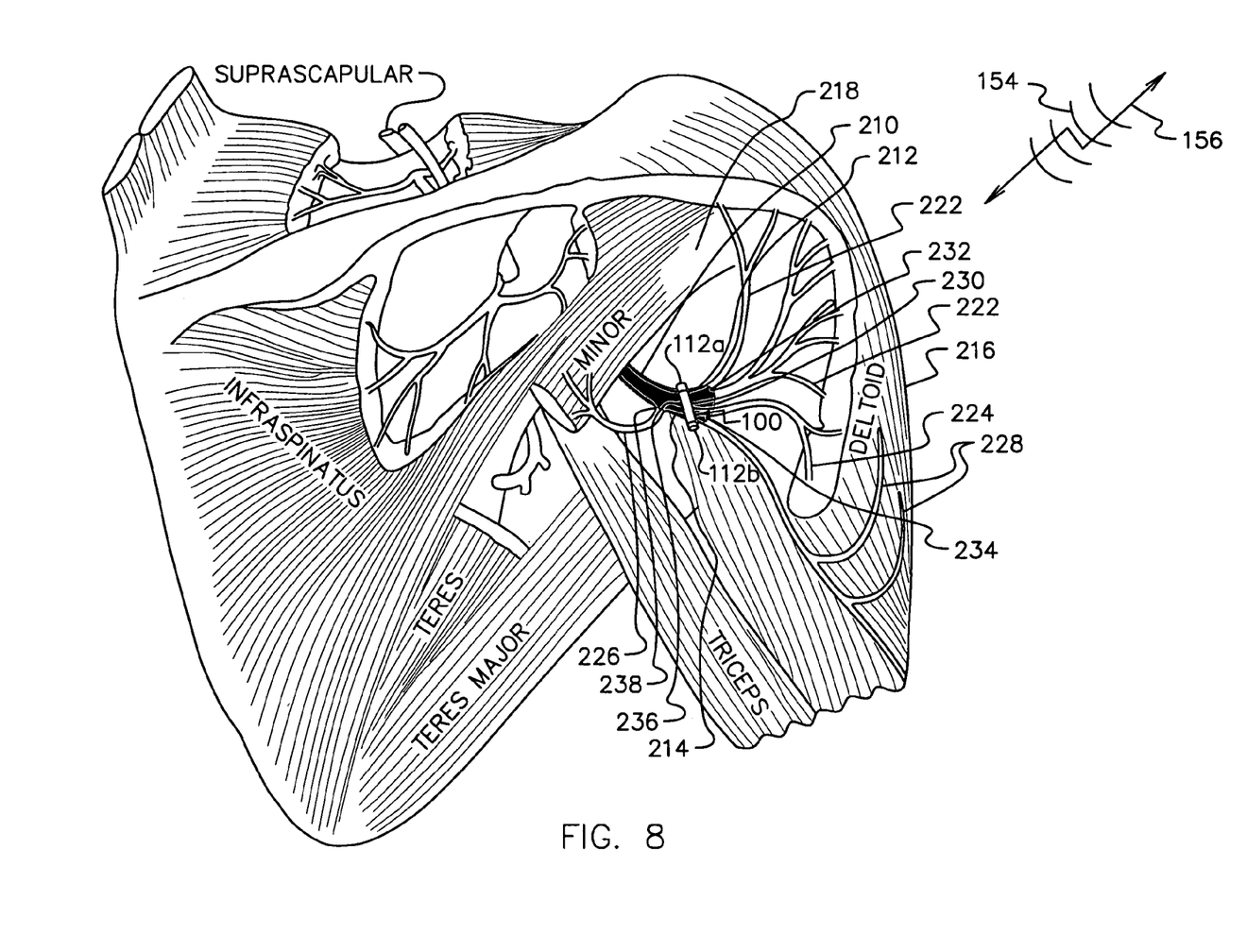
FIG. 8 shows a detailed diagram of the anatomy of a patient's shoulder showing a preferred placement of a single implantable device across branches of the axillary nerve to stimulate the axillary nerve which in turn activates sensory fibers to relieve shoulder pain and activates various portions of the deltoid muscle.

It is notable that FIG. 7 is intended to represent the use of a battery-powered or RF-powered device. Accordingly, the use of a modulated alternating AC magnetic field 154 is shown to power/control the RF-powered device. Alternatively, the use of an alternating AC magnetic field 154 to provide recharging power is shown in combination with an RF control signal 156 (which may be supplied concurrently or at different times). Finally, a '284 type device may be used which does not have a battery and thus uses an externally-supplied alternating AC magnetic field 154 to supply operating power and may concurrently use an externally-supplied RF control signal 156 to control its operation. These alternatives apply to the various combinations shown below in reference to FIG. 10.

The implantation site is preferably selected using an apparatus as described in commonly assigned U.S. Pat. No. 6,829,508 (the '508 patent), which is incorporated herein by reference. The '508 patent describes the use of a introducer 176 (see FIG. 2) which is adapted as described in the '508 patent to have electrical probes at its tip. By placing the introducer 176 in what is anticipated as the desired location, the effectiveness of the location can be tested before the device 100 is actually implanted. Furthermore, the described apparatus and associated methods enable subsequent implantation of the device 100 at what has now been proven to be an effective implantation site.

While it is presently preferred that the implantation be done solely via injection and that the integral electrodes to the implantable device 100 be used to directly supply the stimulation signal to the axillary nerve 210, other techniques are also possible. For example, the use of a nerve cuff or the like, e.g., see U.S. Pat. No. 5,358,514, entitled "Implantable Microdevice With Self-Attaching Electrodes", which is incorporated herein by reference, Peterson electrodes, a leaded implantable device, as described in commonly assigned U.S. Pat. No. 6,738,672, entitled "Miniature Implantable Connectors", which is incorporated herein by reference in its entirety, or the use of an attachment structure as described in commonly assigned U.S. patent application Ser. No. 10/718,836 (the '836 application), entitled "Placement Structure For Facilitating Placement Of An Implantable Device Proximate To Neural/Muscular Tissue For Affecting And/Or Sensing Neural/Muscular Tissue", which is incorporated herein by reference in its entirety. The '836 application describes the use of a structure which captures the implantable device and then using an integral winged portion attaches the combined assembly to the desired portion of the nerve, i.e., in this case, the axillary nerve 210.

Figure 9:
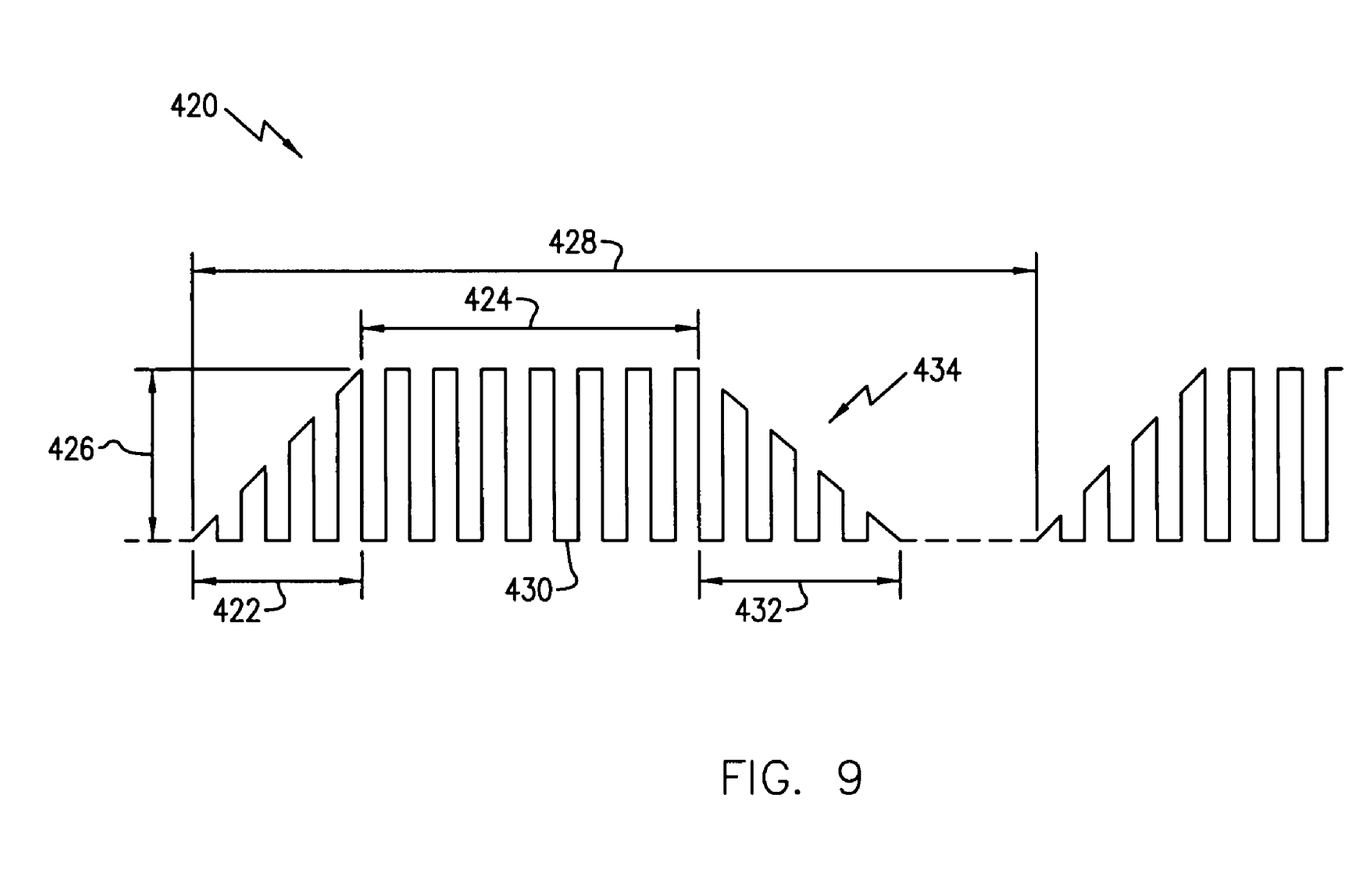
FIG. 9 shows an exemplary stimulus signal pattern emitted by the implanted device to the branches of the axillary nerve, where the predetermined pattern is delivered at a predetermined frequency having a predetermined maximum amplitude, a predetermined ramp up period to a predetermined maximum amplitude, and a predetermined period wherein said pulses are at the predetermined maximum amplitude. With the end of the stimulation train, the pulse amplitudes are ramped down, preventing a sudden drop in the humerous/upper arm.

Once implanted, the device 100 is programmed from an external device, e.g., external device 404, clinician's programmer 172, patient control unit 174, or the like. As described in the '284 patent, various parameters are programmable including the frequency, amplitude, and duration of the stimulation pulses. Additionally, waveforms can be programmed in which a ramp up period is defined, followed by a defined period at a defined amplitude. At the end of the stimulation train, the pulse amplitudes are ramped down, preventing a sudden drop in the humerus/upper arm. This pattern can then be repeated at a prescribed repetition rate. In a presently preferred embodiment (see FIG. 9), a defined ramp up period 422 is shown at a selected frequency 430, a defined period 424 at a maximum amplitude 426, and a defined ramp down period 432. This pattern 434 then repeats at a rate, i.e., after a predefined repetition period 428, defined by the medical practitioner and communicated via the external controller to the implanted device 100.

Figure 10:
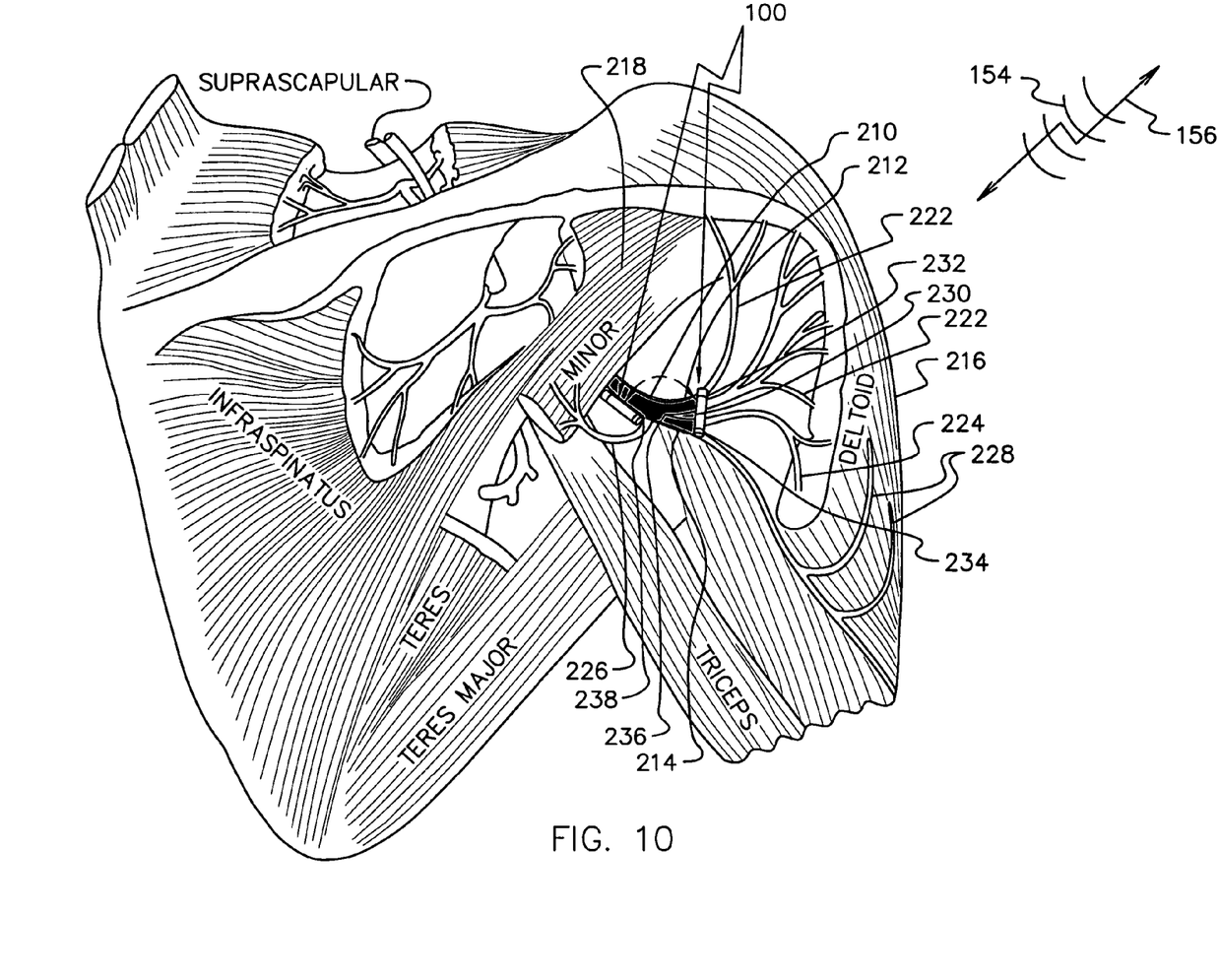
FIG. 10 shows alternative placements of an implantable device for stimulating the axillary nerve of the affected shoulder.

FIG. 10 shows a range of implantation sites within the target stimulation oval shaped area 230, e.g., before the fork 236 where the axillary nerve branches into its anterior 212 and posterior 214 branches, before the fork 238 where axillary nerve branches into a nerve 226 to the teres minor 218, etc. and various other locations in-between within the target stimulation oval shaped area 230 and the target extends to where the axillary nerve originates proximally. While implantation via injection is presently preferred, other implantation techniques, nerve cuffs, attachment assemblies, etc., are also possible as are open surgical procedures. Additionally, in more complex systems, an SCU 302 (see FIG. 2) may control one or more of the devices 100 associated with the present invention instead of an external controller 404.

Accordingly, what has been shown is a method that facilitates treatment of shoulder subluxation by stimulating the axillary nerve (or selected branches of the axillary nerve) of the affected shoulder. While the invention has been described by means of specific embodiments and applications thereof, it is understood that numerous modifications and variations could be made thereto by those skilled in the art without departing from the spirit and scope of the invention. For example, while a single implantable device has been shown to solely treat the effects of shoulder subluxation, the stimulation of the axillary nerve with this implanted device may be a portion of a larger system that provide power and/or control to this axillary nerve stimulator. For example, commonly assigned U.S. patent application Ser. No. 11/004,758 entitled "System And Method Suitable For Treatment Of A Patient With A Neurological Deficit By Sequentially Stimulating Neural Pathways Using A System Of Discrete Implantable Medical Devices", whose contents are incorporated herein by reference in their entirety, describes a system for treatment of a stroke induced hemiplegia affecting one of the patient's arms. It is likely that such a patient would also be subject to the atrophy of the deltoid muscle in the affected arm, and thus shoulder subluxation. In such a case, the master controller of the referenced system could also provide control and/or power to the axillary nerve stimulator of the present application. It is therefore to be understood that within the scope of the claims, the invention may be practiced otherwise than as specifically described herein.

What is claimed is:

1. A method for treating a patient with shoulder subluxation involving weakness and pain comprising the steps of:
   providing an implantable stimulator having at least two electrodes including a cathode and an anode;
   implanting said stimulator via injection at an implantation site at the axillary nerve of the shoulder to which treatment is directed, wherein said implantation site includes an area proximally where the axillary nerve originates to where the axillary nerve branches as the first fork of the anterior branch of the axillary nerve and preceding the first branch of the posterior branch of the anterior nerve where it branches into inferior and cutaneous branches;

providing at least one external controller for wireless transmission of stimulation parameters to said stimulator; and delivering stimulation pulses in accordance with the transmitted stimulation parameters to the axillary nerve.

2. The method of claim 1 further comprising the step of delivering stimulation pulses having a preselected period and preselected maximum amplitude.

3. The method of claim 1 further comprising the step of delivering stimulation pulses comprised of a predetermined pattern at a predetermined frequency having a predetermined maximum amplitude, a predetermined ramp up period to said predetermined maximum amplitude, a predetermined period wherein said pulses are at said predetermined maximum amplitude, and a predetermined ramp down period.

4. The method of claim 1 wherein said step of implanting at least one stimulator comprises using a stimulator which operates off of power provided from an externally-provided magnetic field.

5. The method of claim 1 wherein said step of implanting at least one stimulator comprises using a stimulator which operates off of power from a battery located internal to said stimulator.

6. The method of claim 5 wherein said battery located internal to said stimulator is rechargeable and said method additionally comprises the step of periodically providing an externally-provided magnetic field to cause said internal battery to be recharged.

7. The method of claim 1 wherein said step of implanting said stimulator at an implantation site additionally comprises the step of selecting an implantation site along the axillary nerve from its origins to before the axillary nerve branches into its anterior and posterior branches.

8. The method of claim 1 wherein said step of locating said stimulator at an implantation site additionally comprises the step of selecting an implantation site on the axillary nerve before the axillary nerve branches into a nerve to the teres minor.

9. A method for treating a patient with shoulder subluxation involving weakness and pain comprising the steps of:
locating an implantation site at the axillary nerve of the shoulder to which treatment is to be directed, wherein said implantation site is suitable for activating the patient's deltoid muscle and activating sensory fibers to relieve pain in the patient's shoulder;
implanting a stimulator having at least two electrodes including a cathode and an anode suitable for stimulating the selected axillary nerve, wherein said stimulator with electrodes is implanted via implantation techniques selected from the set of injection and an open surgical procedure; and
remotely programming said implanted stimulator with electrodes to periodically stimulate said selected axillary nerve.

10. The method of claim 9 further comprising the step of delivering stimulation pulses having a preselected period and preselected maximum amplitude.

11. The method of claim 10 wherein said step of delivering stimulation pulses additionally comprises delivering said stimulation pulses at a predetermined pattern and at a predetermined frequency having a predetermined maximum amplitude, a predetermined ramp up period to said predetermined maximum amplitude, a predetermined period wherein said pulses are at said predetermined maximum amplitude, and a predetermined ramp down period.

12. The method of claim 9 wherein said step of implanting said stimulator comprises using a stimulator which operates off of power provided from an externally-provided magnetic field.

13. The method of claim 9 wherein said step of implanting said stimulator comprises using a stimulator which operates off of power from a battery located internal to said stimulator.

14. The method of claim 13 wherein said battery located internal to said stimulator is rechargeable and said method additionally comprises the step of periodically providing an externally-provided magnetic field to cause said internal battery to be recharged.

15. The method of claim 9 wherein said step of locating an implantation site at the axillary nerve of the shoulder to which treatment is to be directed comprises the step of selecting an implantation site proximate to the axillary nerve before the axillary nerve branches into its anterior and posterior branches.

16. The method of claim 9 wherein said step of locating an implantation site at the axillary nerve of the should to which treatment is to be directed comprises the step of selecting an implantation site proximate to the axillary nerve before the axillary nerve branches into a nerve to the teres minor.

17. A method for treating a patient with shoulder subluxation involving weakness and pain comprising the steps of: implanting a device at an implantation site at the axillary nerve of the patient's shoulder needing treatment wherein said site is suitable for activating the patient's deltoid muscle and sensory fibers to relieve pain in the patient's shoulder, and periodically instructing said implanted device from an externally-positioned device to stimulate the selected axillary nerve.

18. The method of claim 17 wherein said method additionally comprises supplying power to said implanted device via an externally-provided AC magnetic field.

19. The method of claim 18 wherein said externally-provided AC magnetic field is modulated with data control instructions to control said implanted device and said step of instructing said implanted device additionally comprises modulating said externally-provided magnetic field with said data control instructions.

20. The method of claim 18 additionally comprising the step of modulating an RF signal with data control instructions to control said implanted device.

21. The method of claim 17 wherein said step of periodically instructing said implanted device comprises the step of causing said implanted device to deliver stimulation pulses comprised of a predetermined pattern at a predetermined frequency having a predetermined maximum amplitude, a predetermined ramp up period to said predetermined maximum amplitude, a predetermined period wherein said pulses are at said predetermined maximum amplitude, and a predetermined ramp down period.

* * * * *